United States Patent
Ishii et al.

(10) Patent No.: US 8,165,362 B2
(45) Date of Patent: Apr. 24, 2012

(54) NEURODEGENERATIVE DISEASE DETECTION METHOD, DETECTING PROGRAM, AND DETECTOR

(75) Inventors: Kazunari Ishii, Himeji (JP); Kiyotaka Watanabe, Nishinomiya (JP); Shuya Miki, Nishinomiya (JP); Kazuo Hamada, Nishinomiya (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 999 days.

(21) Appl. No.: 12/095,474

(22) PCT Filed: Oct. 24, 2006

(86) PCT No.: PCT/JP2006/321138
§ 371 (c)(1),
(2), (4) Date: May 29, 2008

(87) PCT Pub. No.: WO2007/063656
PCT Pub. Date: Jun. 7, 2007

(65) Prior Publication Data
US 2009/0290765 A1    Nov. 26, 2009

(30) Foreign Application Priority Data
Nov. 30, 2005   (JP) .................................. 2005-346190

(51) Int. Cl.
*G06K 9/00*    (2006.01)
(52) U.S. Cl. ...................................................... 382/128
(58) Field of Classification Search .................... 382/128
See application file for complete search history.

(56) References Cited

U.S. PATENT DOCUMENTS
5,027,817 A * 7/1991 John ............................ 600/431
2005/0197560 A1   9/2005 Rao et al.

FOREIGN PATENT DOCUMENTS
| JP | 2003107161 | 4/2003 |
| JP | 2005237441 | 9/2005 |
| JP | 2006204641 | 8/2006 |

OTHER PUBLICATIONS

European Search Report, European Application No. 06822118.3, Dec. 27, 2010, 9 pages.

(Continued)

*Primary Examiner* — W. B. Perkey
(74) *Attorney, Agent, or Firm* — Greenlee Sullivan P.C.

(57) ABSTRACT

A method of detecting a neurodegenerative disease includes (a) a standardization step of creating a first image by applying anatomical standardization to a brain nuclear medical image; (b) a conversion step of creating a second image by converting the pixel value of each pixel of an image based on the first image into a z score or a t value; (c) an addition step of calculating the sum of the pixel values of individual pixels in a predetermined region of interest in the second image; and (d) a detection step of obtaining the results of the detection of the neurodegenerative disease through an operation of comparison of the sum with a predetermined threshold.

33 Claims, 6 Drawing Sheets

OTHER PUBLICATIONS

Ishii K. et al., "Statistical brain mapping of 18F-FDG PET in Alzheimer's disease: Validation of anatomic standardization for atrophied brains," The Journal of Nuclear Medicine 42(4):548-557, Apr. 2001.

Minoshima S. et al., A diagnostic approach in Alzheimer's disease using three-dimensional stereotactic surface projections of fluorine-18-FDG PET, The Journal of Nuclear Medicine 36 (7):1238-1248, Jul. 1995.

International Search Report, International Application No. PCT/JP2006/321138, Jan. 30, 2007, 2 pages.

K. Herholz et al., Discrimination between Alzheimer dementia and controls by automated analysis of multicenter FDG PET, NeuroImage 17:302-316, 2002.

K. Ishii, Clinical application of positron emission tomography for diagnosis of dementia, Annals of Nuclear Medicine 16(8):515-525, 2002.

International Preliminary Report on Patentability, International Application No. PCT/JP2006/321138, Jun. 3, 2008, 6 pages, English Translation.

* cited by examiner

NEURODEGENERATIVE DISEASE DETECTION METHOD, DETECTING PROGRAM, AND DETECTOR

CROSS-REFERENCE TO RELATED APPLICATIONS

This application is the U. S. National Stage of International Application No. PCT/JP2006/321138, filed Oct. 24, 2006, which claims the benefit of Japanese Patent Application JP 2005-346190, filed Nov. 30, 2005, all of which are hereby incorporated by reference to the extent not inconsistent with the disclosure herewith.

TECHNICAL FIELD

The present invention relates to a method of detecting neurodegenerative diseases including Alzheimer's disease, a program and an apparatus for performing the method.

BACKGROUND ART

As the elderly population increases, it is projected to increase the number of patients with degenerative diseases involving dementia including Alzheimer's disease. Since these diseases progress with increasing age to cause the patients and life environments around them to change, it is important to diagnose in the early stages.

Such degenerative diseases involving dementia are mainly diagnosed by diagnostic procedures based on clinical findings such as doctor's questions as typified by Mini Mental Status Examination (hereinafter referred to as "MMSE"). However, the diagnostic procedures based on the clinical findings have low sensitivities in the early stages of symptoms, and the diagnostic outcomes by the diagnostic procedures tend to be affected by cognitive functions innately owned by individuals. Because of such background in the diagnosis for the degenerative diseases, a method is expected which can detect pathologic changes more objectively.

On the one hand, recent researches have revealed that the occurrence of the degenerative diseases involving dementia decreases a glucose metabolism rate partly (for example, see Nonpatent Document 1). Nonpatent Document 2 described below discloses a method of detecting degenerative diseases utilizing this. This method involves comparison of a PET image by administration of 2-[18F]-fluoro-2-deoxy-D-glucose (hereinafter referred to as "FDG") as a tracer for glucose metabolism with that of a normal group to calculate t values of individual pixels, thereby distinguishing a patient with Alzheimer's disease from normals.

[Nonpatent Document 1] Kazunari Ishii, "Clinical application of positron emission tomography for diagnosis of dementia", Annals. of Nuclear Medicine, 2002, 16(8), p. 515-525

[Nonpatent Document 2] K. Herholz et al., "Discrimination between Alzheimer dementia and controls by automated analysis of multicenter FDG PET", NeuroImage, 2002, 17, p. 302-316

DISCLOSURE OF INVENTION

Problems to be Solved by the Invention

For degenerative diseases, a method is expected which can detect pathologic changes in early stages objectively. However, the method disclosed in Nonpatent Document 2 does not define conditions and the like for detecting Alzheimer's disease. The method cannot therefore detect neurodegenerative diseases accurately.

Accordingly, it is an object of the present invention to provide a method and an apparatus for accurately detecting degenerative diseases such as Alzheimer's disease by a brain diagnostic image, and a program for enabling a computer to perform the method.

Means for Solving the Problem

As a result of extensive study, the inventors have discovered that the neurodegenerative disease can be detected based on a comparison of the sum of t values or the sum of z scores of individual pixels in a predetermined region of interest with a threshold based on a normal value (hereinafter referred to as merely "threshold"), and have accomplished the present invention.

A method of detecting a neurodegenerative disease in accordance with an aspect of the present invention includes (a) a standardization step of creating a first image by applying anatomical standardization to a brain nuclear medical image; (b) a conversion step of creating a second image by converting the pixel value of each pixel of an image based on the first image into a z score or a t value; (c) an addition step of calculating the sum of the pixel values of individual pixels in a predetermined region of interest in the second image; and (d) a determination step of obtaining the results of the determination of the neurodegenerative disease through an operation of comparison of the sum with a predetermined threshold.

In addition, in accordance with another aspect of the present invention, a program of detecting a neurodegenerative disease enables a computer to perform steps (a)-(d) described above.

In accordance with a further aspect of the present invention, a neurodegenerative disease detector includes (a) standardization means of creating a first image by applying anatomical standardization to a brain nuclear medical image; (b) conversion means of creating a second image by converting the pixel value of each pixel of an image based on the first image into a z score or a t value; (c) addition means of calculating the sum of the pixel values of individual pixels in a predetermined region of interest in the second image; and (d) determination means of obtaining the results of the determination of the neurodegenerative disease through an operation of comparison of the sum with a predetermined threshold.

Preferably, the detecting method of the present invention further includes a normalization step of creating a normalized image by normalizing each pixel value of the first image between the standardization step and the conversion step, and the conversion step uses the normalized image as the image based on the first image.

Also preferably, the detecting program of the present invention enables the computer to further perform the normalization step described above, and enables the conversion step to use the normalized image as the image based on the first image.

Also preferably, the neurodegenerative disease detector of the present invention further includes normalization means of creating the normalized image by normalizing each pixel value of the first image, and the conversion means uses the normalized image as the image based on the first image.

Meanwhile, various approaches can be used for the normalization. For example, in a usable approach, the pixel values of all the pixels are divided by the average pixel value in a region where the pixel values substantially do not change by the degenerative disease in a region of the first image. The region where the pixel values substantially do not change by the degenerative disease can include a region corresponding to a primary sensorimotor area.

Regions set by various approaches can also be used as the regions of interest. Preferably, a region set by utilizing values of z scores can be used by comparison of a certain number of patients (hereinafter referred to as "disease group") with a certain number of normals (hereinafter referred to as "normal group") through brain nuclear medical images of the individuals in the disease group and brain nuclear medical images of the individuals in the normal group.

More specifically, a region can be preliminarily set as the region of interest by extracting pixels having a z score of three or more obtained by comparison of a disease group having a certain number of individuals with a normal group having a certain number of individuals; forming clusters from pixels adjacent to one another among the extracted pixels; and forming the region by extracting the outline of a cluster having the largest size among the formed clusters.

A value set by the approach described below can be used as the threshold for detection of a neurodegenerative disease. Accordingly, when a z score is assigned to a pixel in the second image, a threshold S that can be used is derived from the following Formula (1):
[Formula (1)]

$$S = Anz + C \cdot SDnz \qquad (1)$$

In the Formula (1), S is the threshold, Anz is the average sum of z scores in the region of interest in the second image of normals, SDnz is the standard deviation of the sum of z scores in the region of interest in the second image of the normals, and C is a constant between 1.5 and 2.5.

In addition, when a t value is assigned to a pixel in the second image, a threshold S that can be used is derived from the following Formula (2):
[Formula (2)]

$$S = Ant + C \cdot SDnt \qquad (2)$$

In the Formula (2), S is the threshold, Ant is the average sum of t values in the region of interest in the second image of normals, SDnt is the standard deviation of the sum of t values in the region of interest in the second image of the normals, and C is a constant between 1.5 and 2.0.

Databases of brain nuclear medical images in normals can be used for calculation of these thresholds. More preferably, each of the constants C in the Formulas (1) and (2) is in the range of 1.5 to 1.6.

Various images can be used for the brain nuclear medical images described above. For example, SPECT and PET images can be used by administration of various radioactive diagnostic agents. Radioactive diagnostic agents preferably used include cerebral blood flow agents, receptor-mapping agents, and various diagnostic agents that can image vital functions such as glucose metabolism. For example, preferably used are SPECT images by administration of diagnostic cerebral blood flow agents such as hydrochloric acid N-isopropyl-4-[123I]iodoamphetamine (Trade name: Perfusamine (Registered trademark), made by Nihon Medi-Physics Co., Ltd., hereinafter referred to as "IMP") and technetium Tc-99m exametazime (Trade name: Cerebrotec (Registered trademark) kit, made by Nihon Medi-Physics Co., Ltd.), and PET images by administration of FDG (hereinafter referred to as "FDG-PET").

The present invention can also detect various degenerative diseases as objects, and typically detect dementia of the Alzheimer's type and Alzheimer's disease as objects.

The region of interest described above can be preliminarily set as a region formed by extracting a pixel having a Z score of 1.5 or more obtained by comparison of a first disease group including a certain number of individuals with a normal group including a certain number of individuals; forming clusters from pixels adjacent to one another among the extracted pixels; selecting a cluster having the largest size among the formed clusters as a first region cluster; extracting a pixel having a Z score of 1.5 or more by comparison of a second disease group including a certain number of individuals having the same disease type as that of the first disease group or the first disease group with a third disease group including a certain number of individuals having a disease type different from that of the first disease group; forming clusters from pixels adjacent to one another among the extracted pixels; selecting a cluster having the largest size among the formed clusters as a second region cluster; forming a third region cluster from common pixels in the first region cluster and the second region cluster; and extracting the outline of the third region cluster.

In this case, a value set by the approach described below can be used as the threshold for detection of a neurodegenerative disease. Accordingly, when a z score is assigned to a pixel in the second image, a threshold S that can be used is derived from the following Formula (3):
[Formula (3)]

$$S = Anz2 + C \cdot SDnz2 \qquad (3)$$

In the Formula (3), S is the threshold, Anz2 is the average sum of z scores in the region of interest in the second image of normals, SDnz2 is the standard deviation of the sum of z scores in the region of interest in the second image of the normals, and C is a constant between 1.5 and 1.6.

In addition, when a t value is assigned to a pixel in the second image, a threshold S that can be used is derived from the following Formula (4):
Formula (4)

$$S = Ant2 + C \cdot SDnt2 \qquad (4)$$

In the Formula (4), S is the threshold, Ant2 is the average sum of t values in the region of interest in the second image of normals, SDnt2 is the standard deviation of the sum of t values in the region of interest in the second image of the normals, and C is a constant between 1.5 and 1.6.

As described above, when a plurality of disease types is treated, objects to be detected in the present invention can include Dementia with Lewy body as the disease type of first and second disease groups, Alzheimer's disease as the disease type of the third disease group, and Dementia with Lewy body as the neurodegenerative disease.

Advantages

A detecting method, a detecting program, and a detector in accordance with the present invention can be used for accurate detection of degenerative diseases such as Alzheimer's disease.

BRIEF DESCRIPTION OF THE DRAWINGS

FIGS. 5(a), 5(b), 5(c), and 5(d) show a right lateral, a left lateral, a right medial, and a left medial, respectively.

FIGS. 6(a), 6(b), 6(c), and 6(d) show a right lateral, a left lateral, a right medial, and a left medial, respectively.

Figure 1:
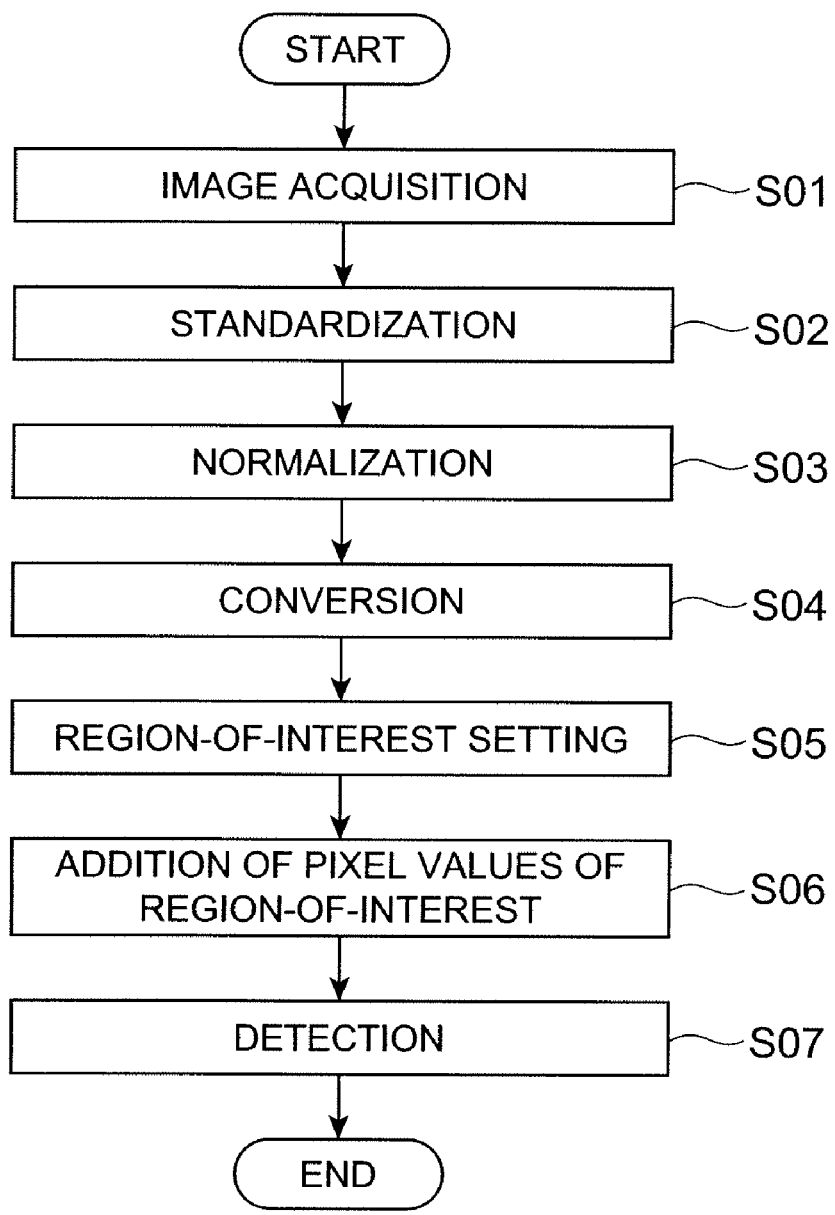
FIG. 1 is a flowchart showing a processing flow of a method of detecting neurodegenerative diseases in accordance with an embodiment of the present invention.

DESCRIPTION OF REFERENCE NUMERALS 300 neurodegenerative disease detector
310 input unit
320 standardization unit
320 image standardization unit
330 normalization unit
340 conversion unit
350 setting unit for region of interest
360 addition unit
370 detecting unit
380 output unit

BEST MODE FOR CARRYING OUT THE INVENTION

An embodiment of a method of detecting a degenerative disease in accordance with the present invention will be described below with reference to the drawings in detail. However, the following embodiments merely relate to the best mode, and the present invention should not be limited to the description below.

FIG. 1 is a flowchart showing a processing flow of a method of detecting a neurodegenerative disease in accordance with an embodiment of the present invention. The detecting method in FIG. 1 first acquires a brain nuclear medical image of an examinee to be detected (Step S01). For example, SPECT and PET images can be used as the brain nuclear medical images by administration of various radioactive diagnostic agents. When a degenerative disease to be detected is Alzheimer's disease, an FDG-PET image can be preferably used as the brain nuclear medical image. These images can be acquired in known ways.

The brain nuclear medical image described above just has to be stored in a data format readable by computers. For example, a brain nuclear medical image can be used that is stored as data in DICOM format. For example, this data can also be provided in the form of the data that is stored in a storage medium such as a compact disc and is readable by a computer. The storage medium storing the data is inserted into a data reader equipped in the computer, thereby the computer reading out the data. Then, the computer can process the brain nuclear medical image. In addition, the data may be directly acquired as computer data signals superimposed on carrier waves through a network.

Next, anatomical standardization is applied to the acquired brain nuclear medical image to convert the brain nuclear medical image into that of a standard brain (standardization step S02), thereby creating a first image. Any known process can be used for the anatomical standardization.

The anatomical standardization includes, for example, a step of conforming the tilt of brain nuclear medical image of the examinee to that of the standard brain; a step of applying linear transformation to the brain nuclear medical image after the tilt correction to conform the shape of the brain nuclear medical image to that of the standard brain; and a step of applying nonlinear transformation to the brain nuclear medical image after the linear transformation to adjust the shape.

For example, the step of conforming to the tilt can utilize a process of conforming to an AC-PC line (for example, see S. Minoshima et al., J. Nucl. Med., 1993, 34, p. 322-9, and S. Minoshima et al., J. Nucl. Med., 1994, 35, p. 1528-37), and maximization of mutual information (see F. Maes et al., IEEE Trans. Med. Img., 1997, 16(2), p. 187-198). The linear transformation can also utilize known processes (for example, see S. Minoshima et al., J. Nucl. Med., 1994, 35, p. 1528-37). The nonlinear transformation can also utilize known processes (for example, see S. Minoshima et al., J. Nucl. Med., 1994, 35, p. 1528-37).

For example, the anatomical standardization can also be performed by SPM (Friston K. J. et al., Human Brain Mapping, 1995, 2, p. 189-210), and 3D-SSP (Minoshima S. et. al., J. Nucl. Med., 1994, 35, p. 1528-37). These processes can be performed through known programs such as SPM (available from Institute of Neurology, University College London), NEUROSTAT (available from Satoshi Minoshima, professor at University of Washington Medical School, and from Nihon Medi-Physics Co., Ltd. as "iNEUROSTAT Revision2").

Next, the detecting method normalizes the pixel values of the first image to eliminate the fluctuation in the pixel values caused by the dosage and imaging conditions, for example, thereby creating a normalized image (normalization step S03). The normalization step preferably extracts a region in which the pixel values substantially do not change by the degenerative disease from the first image to divide the pixel values of all the pixels of the first image by the average pixel value in the region, thereby creating the normalized image. A region corresponding to the primary sensorimotor area can be preferably used as the region in which the pixel values substantially do not change by the degenerative disease. The region can be defined by predetermined coordinates on the standard brain.

After the normalization step is completed, the pixel value of each pixel of the normalized image is converted into a z score or at value, thereby creating a second image (conversion step S04). The conversion into the z score or t value can be performed by known processes. A process of converting the pixel value into a z score will be described below.

Figure 2:
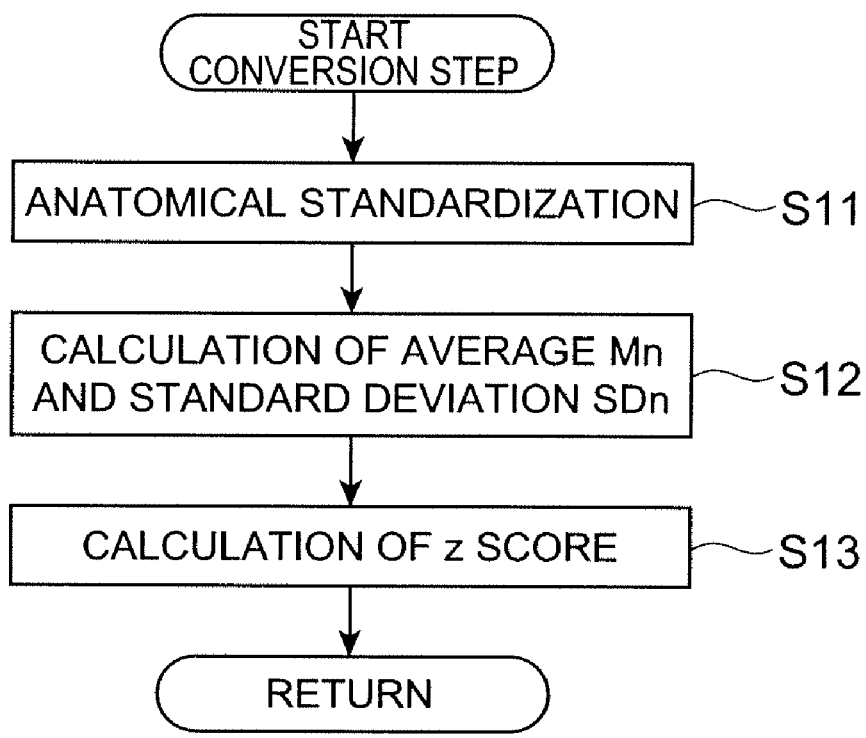
FIG. 2 is a flowchart showing a processing flow in a conversion step in accordance with an embodiment of the present invention.

FIG. 2 is a flowchart illustrating a processing flow in the conversion step in accordance with an embodiment of the present invention. In this embodiment, a plurality of brain nuclear medical images of normals is first converted into a standard brain by anatomical standardization, thereby creating a plurality of first images (Step S11).

Next, the plurality of first images obtained by Step S11 is normalized into a plurality of normalized images to calculate the averages Mn and the standard deviations SDn of the pixel values of all the pixels of the normalized images (Step S12). Meanwhile, the normalization can be performed by dividing the pixel values of all the pixels of the first image by the average pixel value in a region corresponding to the primary sensorimotor area in the first image.

Next, the following Formula (e1) is operated using the average Mn and the standard deviation SDn found in Step S12 to determine the z score (Step S13). Ip in the Formula (e1)

indicates the pixel value of each pixel of the normalized image as an object to detect the degenerative disease.

[Formula (5)]

$$z = \frac{M_n - I_p}{SD_n} \tag{e1}$$

Meanwhile, the average Mn and the standard deviation SDn may be calculated every conversion step, or may be calculated preliminarily. In the latter case, the average Mn and the standard deviation SDn calculated preliminarily are stored in a storage medium to use these values for the operation described above.

Next, returning to FIG. 1, the detecting method sets a region of interest in a second image (Step S05). The region of interest can be set by applying predetermined region data set as coordinate data on the standard brain to the second image.

The region of interest may be a region preliminarily set by comparison of a disease group with a normal group. The most preferred embodiment can use a region set by utilizing the values of z scores by comparison of a disease group including a certain number of individuals with a normal group including a certain number of individuals as the region of interest.

Specifically, the following process can determine the region of interest. First, pixels having a z score of three or more are extracted by comparison of the disease group having a certain number of individuals with the normal group having a certain number of individuals. Next, clusters are formed from pixels adjacent to one another among the extracted pixels to select a cluster having the largest size among the resulting clusters. The region of interest can be set using a region indicating the substantially same site as the selected cluster. Meanwhile, the region of interest can be defined as the coordinate data of its outline.

The z score by the group comparison described above can be determined by any known process. For example, the following Formula (e2) is operated to calculate the t value, applying the found t value and the degree of freedom (Nn+Na−2) to the t distribution table to determine a p value. Thereafter, this p value is applied to the normal distribution table to determine the z score by the group comparison.

[Formula (6)]

$$t = \frac{|M_n - M_a|}{\sqrt{\frac{SD_n^2 \cdot N_n + SD_a^2 \cdot N_a}{N_n + N_a - 2}\left(\frac{1}{N_n} + \frac{1}{N_a}\right)}} \tag{e2}$$

In the Formula (e2), Mn is the average pixel value of each pixel in the normal group, Ma is the average pixel value of each pixel in the disease group, SDn is the standard deviation of the pixel value of each pixel in the normal group, SDa is the standard deviation of the pixel value of each pixel in the disease group, and Nn and Na are the number of samples in the normal group and the disease group, respectively.

Next, returning to FIG. 1, the detecting method calculates the sum of the z scores of individual pixels in the predetermined region of interest in the second image (addition step S06).

Next, the sum calculated in the addition step is compared with a predetermined threshold to detect the degenerative disease (detection step S07). Specifically, when the sum of the z scores calculated in the addition step is larger than the predetermined threshold, the corresponding brain nuclear medical image is detected as the brain nuclear medical image of the degenerative disease.

In a preferred embodiment, the threshold used in the detection step is determined with the data of the normal group. Specifically, the above-described conversion into the z score is applied to each normalized image in the normal group to obtain the second image, and to calculate the sum of the z scores of all the pixels in the region of interest in the second image. Then, the average and the standard deviation of the sum in the normal group are calculated to operate the following Formula (1) using the average and the standard deviation, thereby determining the threshold.

[Formula (7)]

$$S = Anz + C \cdot SDnz \tag{1}$$

In the Formula (1), S is the threshold, Anz is the average sum of z scores in the region of interest of normals, SDnz is the standard deviation of the sum of z scores in the region of interest of the normals, and C is a constant, for example, between 1.5 and 2.5.

In addition, when the t value is assigned to a pixel in the second image, the threshold S that can be used is derived from the following Formula (2):

[Formula (8)]

$$S = Ant + C \cdot SDnt \tag{2}$$

In the Formula (2), S is the threshold, Ant is the average sum of t values in the region of interest in the second image of normals, SDnt is the standard deviation of the sum of t values in the region of interest in the second image of the normals, and C is a constant, for example, between 1.5 and 2.0.

In the Formulas (1) and (2), the constants C are preferably in the range of 1.5 to 2.0, more preferably, in the range of 1.5 to 1.6, and still more preferably, 1.6. Smaller constants C cause decreased specificity in detection of the degenerative disease, which is not preferable. Larger constants C cause decreased sensitivity, which is not preferable.

Figure 3:
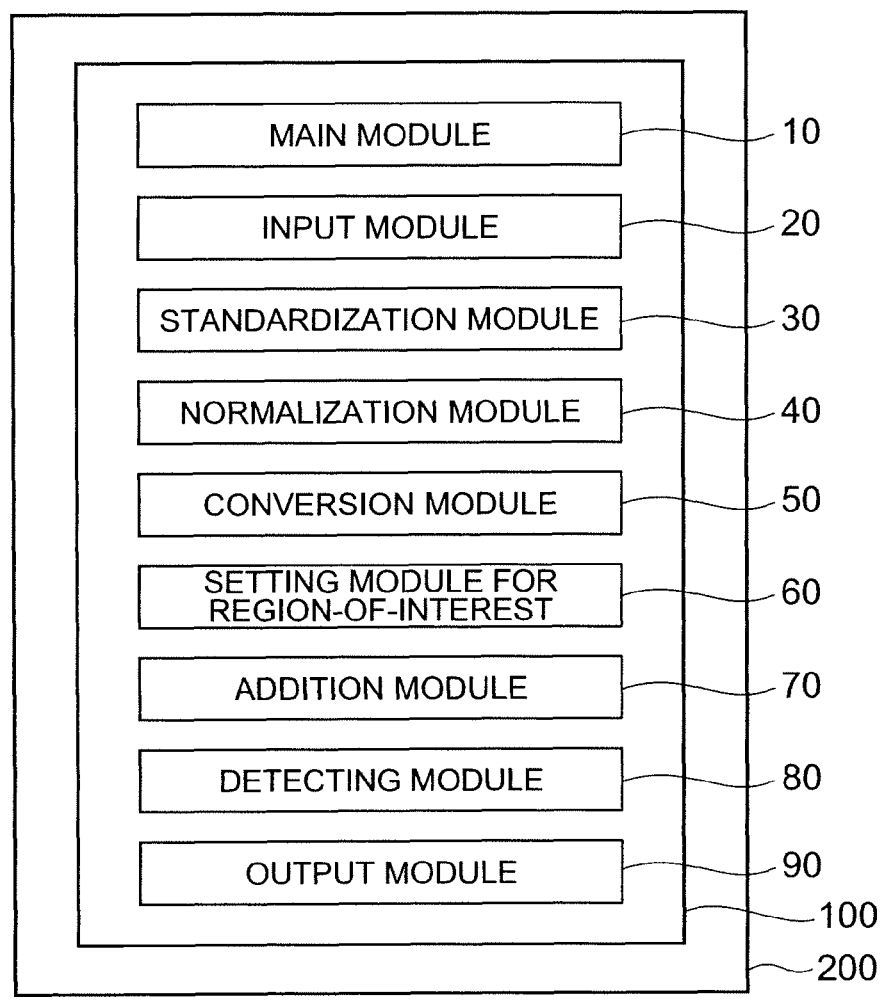
FIG. 3 is a block diagram showing a program of detecting neurodegenerative diseases in accordance with an embodiment of the present invention, together with a recording medium.

Next, an embodiment of a program of detecting a neurodegenerative disease in accordance with the present invention will be described. FIG. 3 is a block diagram showing the program of detecting neurodegenerative diseases in accordance with this embodiment of the present invention, together with a recording medium.

The program 100 of detecting neurodegenerative diseases shown in FIG. 3 is provided in the form that is stored in a recording medium 200. The examples of the recording medium 200 include a floppy disk, a hard disk, other recording media such as a CD-ROM, a DVD, and other ROMs, and a semiconductor memory.

The recording medium 200 storing the detecting program 100 is inserted into a data reader equipped in a computer, so that the computer can access the detecting program 100 and can operate as a neurodegenerative disease detector by the detecting program 100.

As shown in FIG. 3, the detecting program 100 includes a main module 10 controlling overall processes, an input module 20, a standardization module 30, a normalization module 40, a conversion module 50, a setting module 60 for the region of interest, an addition module 70, a detecting module 80, and an output module 90.

The input module 20 enables the computer to perform the process in accordance with Step S01 described above. The standardization module 30 enables the computer to perform the process in accordance with Step S02. The normalization module 40 enables the computer to perform the process in accordance with Step S03. The conversion module 50 enables the computer to perform the process in accordance with Step S04. The setting module 60 for the region of interest enables the computer to perform the process in accordance with Step S05. The addition module 70 enables the computer to perform the process in accordance with Step S06. The detecting module 80 enables the computer to perform the process in accordance with Step S07. The output module 90 outputs the results of the detection of the neurodegenerative disease (i.e. whether the neurodegenerative disease is detected in the brain nuclear medical image as an object or not) to an output device such as a display device.

Figure 4:
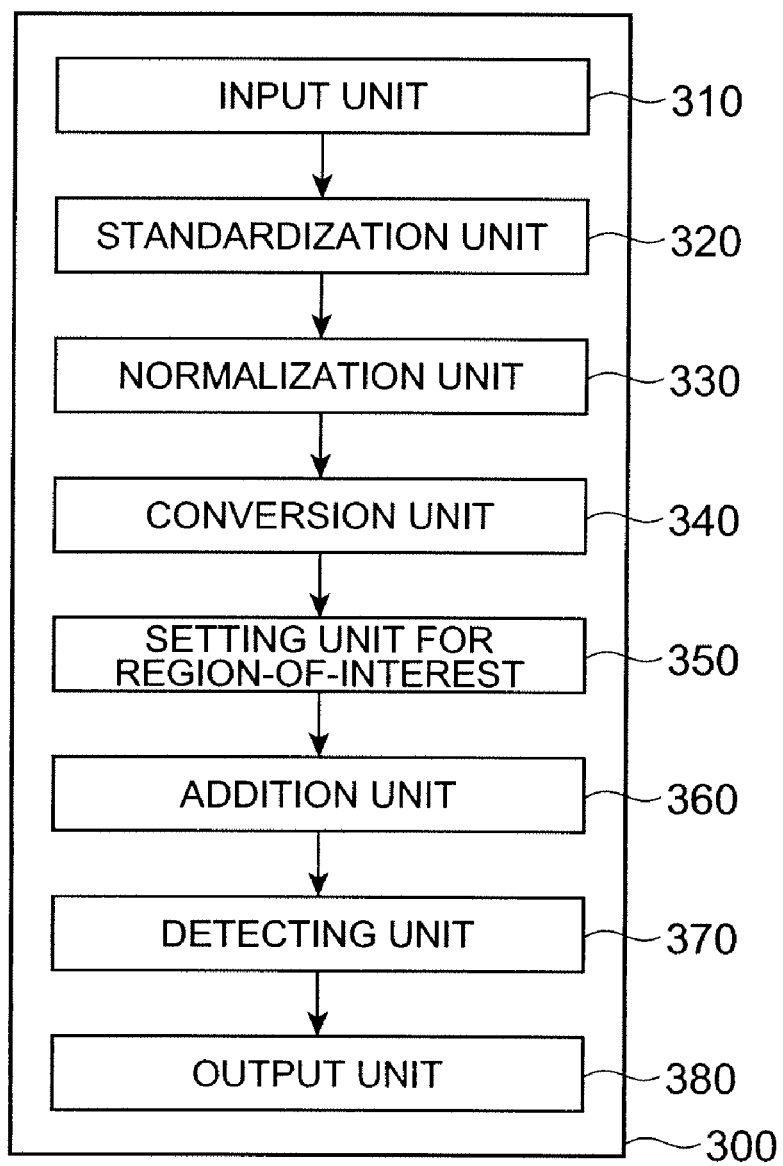
FIG. 4 is a block diagram showing a neurodegenerative disease detector in accordance with an embodiment of the present invention.

Next, an embodiment of a neurodegenerative disease detector in accordance with the present invention will be described. FIG. 4 is a block diagram showing the neurodegenerative disease detector in accordance with this embodiment of the present invention. The neurodegenerative disease detector 300 shown in FIG. 4 functionally includes an input unit 310, a standardization unit 320, a normalization unit 330, a conversion unit 340, a setting unit 350 for the region of interest, an addition unit 360, a detecting unit 370, and an output unit 380.

The input unit 310 is a component that performs the process in accordance with Step S01 described above. The image standardization unit 320 is a component that performs the process in accordance with Step S02. The normalization unit 330 is a component that performs the process in accordance with Step S03. The conversion unit 340 is a component that performs the process in accordance with Step S04. The setting unit 350 for the region of interest is a component that performs the process in accordance with Step S05. The addition unit 360 is a component that performs the process in accordance with Step S06. The detecting unit 370 is a component that performs the process in accordance with Step S07. The output unit 380 is a component that outputs the results of the detection of the neurodegenerative disease (i.e. whether the neurodegenerative disease is detected in the brain nuclear medical image as an object or not) to an output device such as a display device.

EXAMPLE 1

The present invention will now be described in more detail by way of Examples. However, the present invention should not be limited to these Examples.

[Setting the Region of Interest]
The region of interest was set using a normal group (hereinafter referred to as "normal group A") consisting of twenty brain PET image examples obtained by administration of FDG to normals and a disease group (hereinafter referred to as "disease group A") consisting of twenty brain PET image examples obtained by administration of FDG to patients diagnosed as "probable Alzheimer's disease" by the diagnostic criterion of NINCDS/ADRDA (National Institute of Neurological and Communicative Disorders and Strokes-Alzheimer's Disease and Related Disorders Association).

First, the anatomical standardization and brain surface extraction of the data (hereinafter referred to as merely "anatomical standardization") by NEUROSTAT program (iNEUROSTAT version2, available from Nihon Medi-Physics Co., Ltd.) were applied to the brain PET images of the normal group A and the disease group A. Next, these first images obtained by the anatomical standardization were used to compare the normal group A with the disease group A for every pixel based on the Formula (e2) and to calculate the t value. Meanwhile, Nn and Na in the Formula (e2) were the number of samples in the normal group A and the disease group A, namely twenty, respectively.

Figure 5:
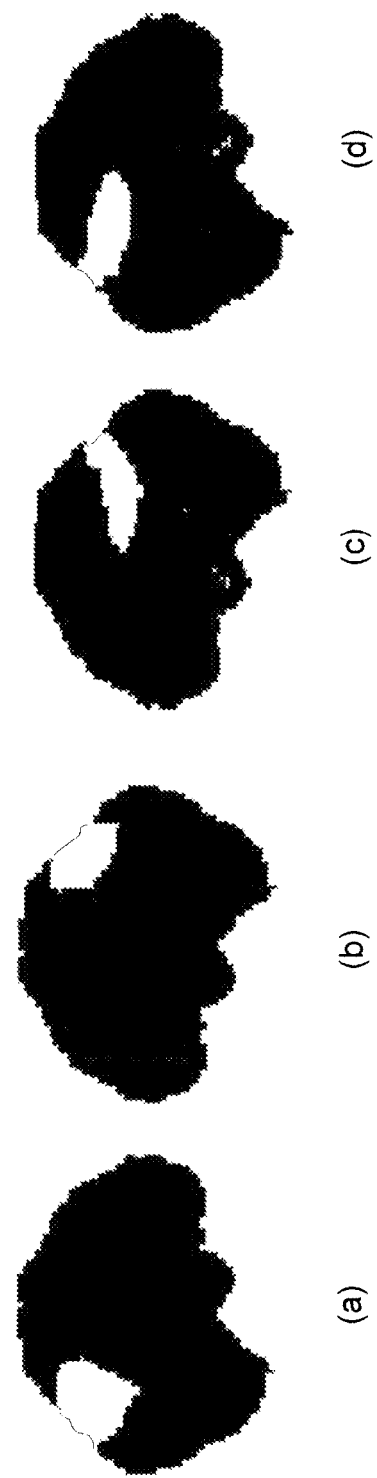
FIG. 5 shows a region of interest set on a standard brain for a diagnosis for Alzheimer's disease.

The resulting t value and the degree of freedom (=18) were applied to the t distribution table to determine the p value. Thereafter, this p value was applied to the normal distribution table to determine the z score of each pixel. Next, pixels having a z score of three or more were extracted to set the region of interest by surrounding the outer edge of the largest cluster in each area of a left lateral, a right lateral, a left medial, and a right medial. FIG. 5 shows the set region of interest. FIGS. 5($a$), 5($b$), 5($c$), and 5($d$) show the regions of interest of the right lateral, the left lateral, the right medial, and the left medial, respectively.

[Setting the Threshold]
A normalized image was created from each first image obtained by the anatomical standardization for the normal group A, and a second image was created from each normalized image. Next, the region of interest found as described above was set on each created second image to calculate the sum of the z scores in the region of interest and to determine the average and the standard deviation of the sum of the overall normal group A. The resulting average Anz and standard deviation SDnz were used to determine the threshold S based on the above-described Formula (1) with a constant C in the range of 1.5 to 2.0.

[Detecting Alzheimer's Disease]
Alzheimer's disease was detected by the method in accordance with the present invention using a normal group (hereinafter referred to as "normal group B") consisting of fifteen brain PET image examples obtained by administration of FDG to normals and a disease group (hereinafter referred to as "disease group B") consisting of fifteen brain PET image examples obtained by administration of FDG to patients diagnosed as "probable" by the diagnostic criterion of NINCDS/ADRDA, estimating the sensitivity and the specificity.

The anatomical standardization by NEUROSTAT program (iNEUROSTAT version2, available from Nihon Medi-Physics Co., Ltd.) was applied to each brain PET image of the normal group B and the disease group B to create the first image corresponding to each brain PET image. The average pixel value in a region corresponding to the primary sensorimotor area was determined for each created first image to divide the pixel values of all the pixels by the average, thereby obtaining a normalized image. Next, Formula (e1) was operated for each normalized image to obtain a second image.

Next, the region of interest found as described above was set on each second image to determine the sum of the z scores in the region of interest of each of the left lateral, the right lateral, the left medial, and the right medial. The resulting sum of the z scores was compared with the threshold found as described above to extract an image having a sum exceeding the threshold in any of the left lateral, the right lateral, the left medial, and the right medial as Alzheimer's disease.

The images extracted as Alzheimer's disease in the disease group and the images not extracted as Alzheimer's disease in the normal group were set to be true, and all remaining images were false to sort each brain PET image. Tables 1 to 3 show the result.

TABLE 1

The result when the threshold is set to the average + 1.5 SD

| | Left lateral surface | Right lateral surface | Left medial surface | Right medial surface | Result |
|---|---|---|---|---|---|
| Threshold (=average + 1.5 SD) | 156793 | 102849 | 113850 | 93318.17 | |
| DISEASE Image 1 | 432247 | 425544 | 251594 | 285058 | True |

TABLE 1-continued

The result when the threshold is set to the average + 1.5 SD

|  |  | Left lateral surface | Right lateral surface | Left medial surface | Right medial surface | Result |
|---|---|---|---|---|---|---|
| GROUP B | Image 2 | 576444 | 486725 | 210287 | 311998 | True |
|  | Image 3 | 388561 | 350352 | 295319 | 247056 | True |
|  | Image 4 | 127184 | 193240 | 37157 | 103063 | True |
|  | Image 5 | 479693 | 293936 | 190258 | 153720 | True |
|  | Image 6 | 41900 | 144113 | 3981 | 13220 | True |
|  | Image 7 | 396583 | 164793 | 216376 | 127294 | True |
|  | Image 8 | 82933 | 41750 | 87207 | 53679 | False |
|  | Image 9 | 376103 | 205861 | 250683 | 162123 | True |
|  | Image 10 | 213653 | 211285 | 153970 | 155291 | True |
|  | Image 11 | 544225 | 139913 | 244718 | 158681 | True |
|  | Image 12 | 498473 | 102168 | 195608 | 106338 | True |
|  | Image 13 | 164091 | 116825 | 91147 | 101112 | True |
|  | Image 14 | 562241 | 266747 | 270738 | 154192 | True |
|  | Image 15 | 166197 | 66629 | 107596 | 54041 | True |
| NORMAL | Image 16 | 24422 | 102 | 0 | 0 | True |
| GROUP B | Image 17 | 170700 | 96450 | 66039 | 65893 | False |
|  | Image 18 | 105863 | 22056 | 4954 | 9123 | True |
|  | Image 19 | 11529 | 13259 | 7441 | 18792 | True |
|  | Image 20 | 32963 | 14506 | 7664 | 9563 | True |
|  | Image 21 | 59466 | 47160 | 79671 | 77548 | True |
|  | Image 22 | 3647 | 557 | 17 | 0 | True |
|  | Image 23 | 19681 | 21641 | 2876 | 807 | True |
|  | Image 24 | 58704 | 45690 | 7725 | 15071 | True |
|  | Image 25 | 69708 | 3654 | 42445 | 4004 | True |
|  | Image 26 | 434 | 385 | 5182 | 0 | True |
|  | Image 27 | 7026 | 96 | 546 | 0 | True |
|  | Image 28 | 2733 | 0 | 20119 | 5383 | True |
|  | Image 29 | 55887 | 27871 | 52889 | 33436 | True |
|  | Image 30 | 49772 | 66111 | 52209 | 51257 | True |

(SD indicates the standard deviation in the table)

TABLE 2

The result when the threshold is set to the average + 1.64 SD

|  |  | Left lateral surface | Right lateral surface | Left medial surface | Right medial surface | Result |
|---|---|---|---|---|---|---|
| Threshold (=average + 1.64 SD) |  | 166045.4 | 108456.4 | 120724.1 | 99004.12 |  |
| DISEASE | Image 1 | 432247 | 425544 | 251594 | 285058 | True |
| GROUP B | Image 2 | 576444 | 486725 | 210287 | 311998 | True |
|  | Image 3 | 388561 | 350352 | 295319 | 247056 | True |
|  | Image 4 | 127184 | 193240 | 37157 | 103063 | True |
|  | Image 5 | 479693 | 293936 | 190258 | 153720 | True |
|  | Image 6 | 41900 | 144113 | 3981 | 13220 | True |
|  | Image 7 | 396583 | 164793 | 216376 | 127294 | True |
|  | Image 8 | 82933 | 41750 | 87207 | 53679 | False |
|  | Image 9 | 376103 | 205861 | 250683 | 162123 | True |
|  | Image 10 | 213653 | 211285 | 153970 | 155291 | True |
|  | Image 11 | 544225 | 139913 | 244718 | 158681 | True |
|  | Image 12 | 498473 | 102168 | 195608 | 106338 | True |
|  | Image 13 | 164091 | 116825 | 91147 | 101112 | True |
|  | Image 14 | 562241 | 266747 | 270738 | 154192 | True |
|  | Image 15 | 166197 | 66629 | 107596 | 54041 | True |
| NORMAL | Image 16 | 24422 | 102 | 0 | 0 | True |
| GROUP B | Image 17 | 170700 | 96450 | 66039 | 65893 | False |
|  | Image 18 | 105863 | 22056 | 4954 | 9123 | True |
|  | Image 19 | 11529 | 13259 | 7441 | 18792 | True |
|  | Image 20 | 32963 | 14506 | 7664 | 9563 | True |
|  | Image 21 | 59466 | 47160 | 79671 | 77548 | True |
|  | Image 22 | 3647 | 557 | 17 | 0 | True |
|  | Image 23 | 19681 | 21641 | 2876 | 807 | True |
|  | Image 24 | 58704 | 45690 | 7725 | 15071 | True |
|  | Image 25 | 69708 | 3654 | 42445 | 4004 | True |
|  | Image 26 | 434 | 385 | 5182 | 0 | True |
|  | Image 27 | 7026 | 96 | 546 | 0 | True |
|  | Image 28 | 2733 | 0 | 20119 | 5383 | True |
|  | Image 29 | 55887 | 27871 | 52889 | 33436 | True |
|  | Image 30 | 49772 | 66111 | 52209 | 51257 | True |

(SD indicates the standard deviation in the table)

TABLE 3

The result when the threshold is set to the average + 2.0 SD

|  |  | Left lateral surface | Right lateral surface | Left medial surface | Right medial surface | Result |
|---|---|---|---|---|---|---|
| Threshold (=average + 2.0 SD) |  | 189837.4 | 122875.3 | 138400.5 | 113625.1 |  |
| DISEASE | Image 1 | 432247 | 425544 | 251594 | 285058 | True |

TABLE 3-continued

The result when the threshold is set to the average + 2.0 SD

| | | Left lateral surface | Right lateral surface | Left medial surface | Right medial surface | Result |
|---|---|---|---|---|---|---|
| GROUP B | Image 2 | 576444 | 486725 | 210287 | 311998 | True |
| | Image 3 | 388561 | 350352 | 295319 | 247056 | True |
| | Image 4 | 127184 | 193240 | 37157 | 103063 | True |
| | Image 5 | 479693 | 293936 | 190258 | 153720 | True |
| | Image 6 | 41900 | 144113 | 3981 | 13220 | True |
| | Image 7 | 396583 | 164793 | 216376 | 127294 | True |
| | Image 8 | 82933 | 41750 | 87207 | 53679 | False |
| | Image 9 | 376103 | 205861 | 250683 | 162123 | True |
| | Image 10 | 213653 | 211285 | 153970 | 155291 | True |
| | Image 11 | 544225 | 139913 | 244718 | 158681 | True |
| | Image 12 | 498473 | 102168 | 195608 | 106338 | True |
| | Image 13 | 164091 | 116825 | 91147 | 101112 | False |
| | Image 14 | 562241 | 266747 | 270738 | 154192 | True |
| | Image 15 | 166197 | 66629 | 107596 | 54041 | False |
| NORMAL | Image 16 | 24422 | 102 | 0 | 0 | True |
| GROUP B | Image 17 | 170700 | 96450 | 66039 | 65893 | True |
| | Image 18 | 105863 | 22056 | 4954 | 9123 | True |
| | Image 19 | 11529 | 13259 | 7441 | 18792 | True |
| | Image 20 | 32963 | 14506 | 7664 | 9563 | True |
| | Image 21 | 59466 | 47160 | 79671 | 77548 | True |
| | Image 22 | 3647 | 557 | 17 | 0 | True |
| | Image 23 | 19681 | 21641 | 2876 | 807 | True |
| | Image 24 | 58704 | 45690 | 7725 | 15071 | True |
| | Image 25 | 69708 | 3654 | 42445 | 4004 | True |
| | Image 26 | 434 | 385 | 5182 | 0 | True |
| | Image 27 | 7026 | 96 | 546 | 0 | True |
| | Image 28 | 2733 | 0 | 20119 | 5383 | True |
| | Image 29 | 55887 | 27871 | 52889 | 33436 | True |
| | Image 30 | 49772 | 66111 | 52209 | 51257 | True |

(SD indicates the standard deviation in the table)

The sensitivity and the specificity were determined for the case that used each threshold from the results of the sorting. Table 4 shows the results.

TABLE 4

Sensitivity and specificity in the case using each threshold

| Threshold | Sensitivity [%] | Specificity [%] |
|---|---|---|
| Average + 1.5 SD | 93% | 93% |
| Average + 1.64 SD | 93% | 93% |
| Average + 2.0 SD | 80% | 100% |

(SD indicates the standard deviation in the table)

As shown in Table 4, when the threshold is set in the range the average+1.5SD to the average+2.0SD, both the sensitivity and the specificity are satisfactory. Therefore, it is confirmed that the method in accordance with the present invention can detect Alzheimer's disease accurately. Particularly, when the threshold is set to the average+1.5SD and the average+1.64SD, both the sensitivity and the specificity have satisfactory values, i.e., 93%. The average+1.64SD indicates the boundary of data statistically including 95% of normals, supposing the normal distribution. This suggests that the detecting method of Alzheimer's disease in accordance with the present invention can adequately detect this disease in the case of use of an FDG-PET image other than the image used in this example (i.e. an FDG-PET image of a different normal or patient, other than images 1 to 30), like this example.

EXAMPLE 2

[Setting the Region of Interest in the Diagnosis for Dementia with Lewy Body (Hereinafter Referred to as "DLB")]

The region of interest was set using twenty-two brain PET image examples obtained by administration of FDG to normals (hereinafter referred to as "normal group C"), ten brain PET image examples obtained by administration of FDG to patients (hereinafter referred to as "disease group C") diagnosed as "probable" (highly probable DLB) by the diagnostic criterion of DLB (McKeith I G; Garasko D, Kosaka K, et al., Consensus guidelines for the clinical and pathological diagnosis of dementia with Lewy bodies (DLB), Neurology 1996; 47: p. 1113-24) and twenty-two brain PET image examples obtained by administration of FDG to patients (hereinafter referred to as "disease group D") diagnosed as "probable" (highly probable Alzheimer's disease) by the diagnostic criterion of NINCDS/ADRDA (National Institute of Neurological and Communicative Disorders and Strokes-Alzheimer's Disease and Related Disorders Association).

Figure 6:
FIG. 6 shows a region of interest set on a standard brain for a diagnosis for Dementia with Lewy body.

First, the anatomical standardization and brain surface extraction of the data (hereinafter referred to as merely "anatomical standardization") by NEUROSTAT program (iN-EUROSTAT version2, available from Nihon Medi-Physics Co., Ltd.) were applied to these brain PET images. Next, these images obtained by the anatomical standardization were used to compare the normal group C with the disease group C for every pixel and to extract pixels having a z score of 1.5 or more as in Example 1. The outer edge of the largest cluster among the extracted pixels was surrounded in each area of the left lateral, the right lateral, a left medial, and the right medial to set a region of interest 1. Next, the disease group C was also compared with the disease group D by the same process to set a region of interest 2. A common area in the regions of interest 1 and 2 was further extracted to set a region of interest 3 (see FIG. 6). Meanwhile, as described above, the disease type of the disease group C (DLB) is different from that of the disease group D (Alzheimer's disease) in Example 2, which is different from Example 1 in that two disease types are treated. In addition, image examples of different patients can be used as the disease group C for setting the regions of interest 1 and the disease group C for setting the regions of interest 2 as long as these images relate to the same disease type.

[Setting the Threshold]

With each image obtained by the anatomical standardization for the normal group C, the pixel value of each pixel was converted into a z score as in Example 1.

Next, the data of the region of interest 3 set above was assigned to each image to calculate the sum of the z scores of the pixels in the region of interest 3 and to determine the average and the standard deviation of the sum of the overall normal group C. The resulting average and standard deviation were used to determine the threshold as in Example 1.

[Detecting DLB]

DLB was detected by the method in accordance with the present invention using sixteen brain PET image examples obtained by administration of FDG to patients (hereinafter referred to as "disease group E") diagnosed as "probable" by the diagnostic criterion of DLB and twenty-two brain PET image examples obtained by administration of FDG to patients (hereinafter referred to as "disease group F") diagnosed as "probable" by the diagnostic criterion of NINCDS/ADRDA, estimating the sensitivity and the specificity.

The anatomical standardization by NEUROSTAT program (iNEUROSTAT version2, available from Nihon Medi-Physics Co., Ltd.) was applied to each PET image. The pixels corresponding to the primary sensorimotor area was extracted on this image obtained by the anatomical standardization. In addition, the average pixel value of the pixels in this primary sensorimotor area was determined for every image. The pixel value was normalized by the process as in Example 1, thereafter converting the pixel value of each pixel into a z score.

The region of interest set above was applied to this image after the conversion into the z score to determine the sum of the z scores in the region of interest of each of the left lateral, the right lateral, the left medial, and the right medial. The resulting sum of the z scores was compared with the threshold set above to extract an image having a sum exceeding the threshold in any of the left lateral, the right lateral, the left medial, and the right medial as DLB. The images extracted as DLB in the disease group E and the images not extracted as DLB in the disease group F were set to be true, and all remaining images were false to sort these images. Tables 5 to 7 show the result.

TABLE 5

The result when the threshold is set to the average + 1.5 SD

| | | Right Lateral surface | Left lateral surface | Right medial surface | Left medial surface | Result |
|---|---|---|---|---|---|---|
| Threshold (=average + 1.5 SD) | | 621.0638 | 616.0246 | 315.8186 | 270.8185 | |
| DISEASE GROUP E | Image 31 | 621 | 808 | 126 | 237 | True |
| | Image 32 | 966 | 966 | 270 | 321 | True |
| | Image 33 | 1320 | 740 | 378 | 203 | True |
| | Image 34 | 698 | 666 | 192 | 211 | True |
| | Image 35 | 883 | 918 | 255 | 171 | True |
| | Image 36 | 658 | 552 | 239 | 115 | True |
| | Image 37 | 710 | 509 | 187 | 131 | True |
| | Image 38 | 1139 | 1217 | 394 | 452 | True |
| | Image 39 | 159 | 344 | 127 | 134 | False |
| | Image 40 | 1061 | 756 | 320 | 238 | True |
| | Image 41 | 356 | 314 | 75 | 53 | False |
| | Image 42 | 140 | 263 | 52 | 31 | False |
| | Image 43 | 665 | 474 | 147 | 115 | True |
| | Image 44 | 1357 | 1166 | 389 | 425 | True |
| | Image 45 | 854 | 962 | 295 | 374 | True |
| | Image 46 | 542 | 682 | 137 | 161 | True |
| DISEASE GROUP F | Image 47 | 124 | 175 | 74 | 48 | True |
| | Image 48 | 36 | 92 | 13 | 16 | True |
| | Image 49 | 127 | 77 | 56 | 30 | True |
| | Image 50 | 1171 | 721 | 251 | 129 | False |
| | Image 51 | 54 | 132 | 62 | 69 | True |
| | Image 52 | 101 | 58 | 53 | 51 | True |
| | Image 53 | 566 | 126 | 19 | 4 | True |
| | Image 54 | 315 | 538 | 126 | 168 | True |
| | Image 55 | 1628 | 522 | 431 | 195 | False |
| | Image 56 | 116 | 368 | 55 | 84 | True |
| | Image 57 | 130 | 399 | 106 | 130 | True |
| | Image 58 | 898 | 673 | 111 | 67 | False |
| | Image 59 | 51 | 2 | 0 | 0 | True |
| | Image 60 | 273 | 218 | 76 | 78 | True |
| | Image 61 | 303 | 393 | 139 | 129 | True |
| | Image 62 | 569 | 507 | 375 | 342 | False |
| | Image 63 | 320 | 388 | 124 | 177 | True |
| | Image 64 | 234 | 163 | 47 | 66 | True |
| | Image 65 | 162 | 197 | 37 | 30 | True |
| | Image 66 | 472 | 421 | 128 | 106 | True |
| | Image 67 | 401 | 134 | 82 | 25 | True |
| | Image 68 | 129 | 118 | 17 | 38 | True |

(SD indicates the standard deviation in the table)

TABLE 6

The result when the threshold is set to the average + 1.64 SD

|  |  | Right Lateral surface | Left lateral surface | Right medial surface | Left medial surface | Result |
|---|---|---|---|---|---|---|
| | Threshold (=average + 1.64 SD) | 644.0539 | 639.421 | 329.2704 | 282.0342 | |
| DISEASE GROUP E | Image 31 | 621 | 808 | 126 | 237 | True |
| | Image 32 | 966 | 966 | 270 | 321 | True |
| | Image 33 | 1320 | 740 | 378 | 203 | True |
| | Image 34 | 698 | 666 | 192 | 211 | True |
| | Image 35 | 883 | 918 | 255 | 171 | True |
| | Image 36 | 658 | 552 | 239 | 115 | True |
| | Image 37 | 710 | 509 | 187 | 131 | True |
| | Image 38 | 1139 | 1217 | 394 | 452 | True |
| | Image 39 | 159 | 344 | 127 | 134 | False |
| | Image 40 | 1061 | 756 | 320 | 238 | True |
| | Image 41 | 356 | 314 | 75 | 53 | False |
| | Image 42 | 140 | 263 | 52 | 31 | False |
| | Image 43 | 665 | 474 | 147 | 115 | True |
| | Image 44 | 1357 | 1166 | 389 | 425 | True |
| | Image 45 | 854 | 962 | 295 | 374 | True |
| | Image 46 | 542 | 682 | 137 | 161 | True |
| DISEASE GROUP F | Image 47 | 124 | 175 | 74 | 48 | True |
| | Image 48 | 36 | 92 | 13 | 16 | True |
| | Image 49 | 127 | 77 | 56 | 30 | True |
| | Image 50 | 1171 | 721 | 251 | 129 | False |
| | Image 51 | 54 | 132 | 62 | 69 | True |
| | Image 52 | 101 | 58 | 53 | 51 | True |
| | Image 53 | 566 | 126 | 19 | 4 | True |
| | Image 54 | 315 | 538 | 126 | 168 | True |
| | Image 55 | 1628 | 522 | 431 | 195 | False |
| | Image 56 | 116 | 368 | 55 | 84 | True |
| | Image 57 | 130 | 399 | 106 | 130 | True |
| | Image 58 | 898 | 673 | 111 | 67 | False |
| | Image 59 | 51 | 2 | 0 | 0 | True |
| | Image 60 | 273 | 218 | 76 | 78 | True |
| | Image 61 | 303 | 393 | 139 | 129 | True |
| | Image 62 | 569 | 507 | 375 | 342 | False |
| | Image 63 | 320 | 388 | 124 | 177 | True |
| | Image 64 | 234 | 163 | 47 | 66 | True |
| | Image 65 | 162 | 197 | 37 | 30 | True |
| | Image 66 | 472 | 421 | 128 | 106 | True |
| | Image 67 | 401 | 134 | 82 | 25 | True |
| | Image 68 | 129 | 118 | 17 | 38 | True |

(SD indicates the standard deviation in the table)

TABLE 7

The result when the threshold is set to the average + 1.96 SD

|  |  | Right Lateral surface | Left lateral surface | Right medial surface | Left medial surface | Result |
|---|---|---|---|---|---|---|
| | Threshold (=average + 1.96 SD) | 696.6029 | 692.8995 | 360.0174 | 307.6702 | |
| DISEASE GROUP E | Image 31 | 621 | 808 | 126 | 237 | True |
| | Image 32 | 966 | 966 | 270 | 321 | True |
| | Image 33 | 1320 | 740 | 378 | 203 | True |
| | Image 34 | 698 | 666 | 192 | 211 | True |
| | Image 35 | 883 | 918 | 255 | 171 | True |
| | Image 36 | 658 | 552 | 239 | 115 | False |
| | Image 37 | 710 | 509 | 187 | 131 | True |
| | Image 38 | 1139 | 1217 | 394 | 452 | True |
| | Image 39 | 159 | 344 | 127 | 134 | False |
| | Image 40 | 1061 | 756 | 320 | 238 | True |
| | Image 41 | 356 | 314 | 75 | 53 | False |
| | Image 42 | 140 | 263 | 52 | 31 | False |
| | Image 43 | 665 | 474 | 147 | 115 | False |
| | Image 44 | 1357 | 1166 | 389 | 425 | True |
| | Image 45 | 854 | 962 | 295 | 374 | True |
| | Image 46 | 542 | 682 | 137 | 161 | False |
| DISEASE GROUP F | Image 47 | 124 | 175 | 74 | 48 | True |
| | Image 48 | 36 | 92 | 13 | 16 | True |
| | Image 49 | 127 | 77 | 56 | 30 | True |

TABLE 7-continued

The result when the threshold is set to the average + 1.96 SD

|  | Right Lateral surface | Left lateral surface | Right medial surface | Left medial surface | Result |
| --- | --- | --- | --- | --- | --- |
| Image 50 | 1171 | 721 | 251 | 129 | False |
| Image 51 | 54 | 132 | 62 | 69 | True |
| Image 52 | 101 | 58 | 53 | 51 | True |
| Image 53 | 566 | 126 | 19 | 4 | True |
| Image 54 | 315 | 538 | 126 | 168 | True |
| Image 55 | 1628 | 522 | 431 | 195 | False |
| Image 56 | 116 | 368 | 55 | 84 | True |
| Image 57 | 130 | 399 | 106 | 130 | True |
| Image 58 | 898 | 673 | 111 | 67 | False |
| Image 59 | 51 | 2 | 0 | 0 | True |
| Image 60 | 273 | 218 | 76 | 78 | True |
| Image 61 | 303 | 393 | 139 | 129 | True |
| Image 62 | 569 | 507 | 375 | 342 | False |
| Image 63 | 320 | 388 | 124 | 177 | True |
| Image 64 | 234 | 163 | 47 | 66 | True |
| Image 65 | 162 | 197 | 37 | 30 | True |
| Image 66 | 472 | 421 | 128 | 106 | True |
| Image 67 | 401 | 134 | 82 | 25 | True |
| Image 68 | 129 | 118 | 17 | 38 | True |

(SD indicates the standard deviation in the table)

The sensitivity and the specificity were determined for the case that used each threshold from the results of the sorting. Table 8 shows the results.

TABLE 8

Sensitivity and specificity in the case using each threshold

| Threshold | Sensitivity [%] | Specificity [%] |
| --- | --- | --- |
| Average + 1.5 SD | 81.3% | 81.8% |
| Average + 1.64 SD | 81.3% | 81.8% |
| Average + 1.96 SD | 62.5% | 81.8% |

As shown in FIG. 8, when the threshold is set in the range the average+1.5 to the average+1.96SD, both the sensitivity and the specificity are satisfactory. Therefore, it is confirmed that the method in accordance with the present invention can detect DLB accurately. Particularly, when the threshold is set to the average+1.5SD and the average+1.64SD, the sensitivity and the specificity have satisfactory values, i.e., 81.3% and 81.8%, respectively. The average+1.64SD indicates the boundary of data statistically including 95% of normals, supposing the normal distribution. This suggests that the detecting method of DLB in accordance with the present invention can adequately detect DLB in the case of use of an FDG-PET image other than the images used in this example (i.e. an FDG-PET image of a different normal or patient, other than images 31 to 68), like this example.

INDUSTRIAL APPLICABILITY

A detecting method, a detecting program, and a detector in accordance with the present invention can be used for accurate detection of degenerative diseases such as Alzheimer's disease.

The invention claimed is:
1. A method of detecting a neurodegenerative disease, comprising:
a standardization step of creating a first image by applying anatomical standardization to a brain nuclear medical image;
a conversion step of creating a second image by converting the pixel value of each pixel of an image based on the first image into a z score or a t value;
an addition step of calculating the sum of the pixel values of individual pixels in a predetermined region of interest in the second image; and
a detection step of obtaining the results of the detection of the neurodegenerative disease through an operation of comparison of the sum with a predetermined threshold, wherein the region of interest is preliminarily set as a region formed by extracting pixels having a z score of three or more obtained by comparison of a disease group having a certain number of individuals with a normal group having a certain number of individuals; forming clusters from pixels adjacent to one another among the extracted pixels; and selecting a cluster having the largest size among the formed clusters to extract the outline of the selected cluster.

2. The method according to claim 1, further comprising a normalization step of creating a normalized image by normalizing each pixel value of the first image, between the standardization step and the conversion step,
wherein the conversion step uses the normalized image as the image based on the first image.

3. The method according to claim 2, wherein the normalization step creates the normalized image by calculating the average pixel value in a region corresponding to a primary sensorimotor area in the first image to normalize the pixel value of each pixel of the first image using the average.

4. The method according to claim 1, wherein the brain nuclear medical image is an FDG-PET image.

5. The method according to claim 1, wherein the neurodegenerative disease is Alzheimer's disease.

6. A method of detecting a neurodegenerative disease, comprising:
a standardization step of creating a first image by applying anatomical standardization to a brain nuclear medical image;
a conversion step of creating a second image by converting the pixel value of each pixel of an image based on the first image into a z score;

an addition step of calculating the sum of the pixel values of individual pixels in a predetermined region of interest in the second image; and a detection step of obtaining the results of the detection of the neurodegenerative disease through an operation of comparison of the sum with a predetermined threshold, wherein the threshold is set by the following Formula (1) where S is the threshold, Anz is the average sum of the z scores in the region of interest in the second image of normals, SDnz is the standard deviation of the sum of the z scores in the region of interest in the second image of the normals, and C is a constant between 1.5 and 2.5

[Formula (1)]

$$S = Anz + C \cdot SDnz \quad (1).$$

7. The method according to claim 6, wherein the constant C is in the range of 1.5 to 1.6.

8. A method of detecting a neurodegenerative disease, comprising:

a standardization step of creating a first image by applying anatomical standardization to a brain nuclear medical image;

a conversion step of creating a second image by converting the pixel value of each pixel of an image based on the first image into a t value;

an addition step of calculating the sum of the pixel values of individual pixels in a predetermined region of interest in the second image; and a detection step of obtaining the results of the detection of the neurodegenerative disease through an operation of comparison of the sum with a predetermined threshold, wherein the threshold is set by the following Formula (2) where S is the threshold, Ant is the average sum of the t values in the region of interest in the second image of normals, SDnt is the standard deviation of the sum of the t values in the region of interest in the second image of the normals, and C is a constant between 1.5 and 2.0

[Formula (2)]

$$S = Ant + C \cdot SDnt \quad (2).$$

9. The method according to claim 8, wherein the constant C is in the range of 1.5 to 1.6.

10. A method of detecting a neurodegenerative disease, comprising:

a standardization step of creating a first image by applying anatomical standardization to a brain nuclear medical image;

a conversion step of creating a second image by converting the pixel value of each pixel of an image based on the first image into a z score or a t value;

an addition step of calculating the sum of the pixel values of individual pixels in a predetermined region of interest in the second image; and a detection step of obtaining the results of the detection of the neurodegenerative disease through an operation of comparison of the sum with a predetermined threshold, wherein the region of interest is preliminarily set as a region formed by extracting a pixel having a Z score of 1.5 or more obtained by comparison of a first disease group including a certain number of individuals with a normal group including a certain number of individuals; forming clusters from pixels adjacent to one another among the extracted pixels; selecting a cluster having the largest size among the formed clusters as a first region cluster; extracting a pixel having a Z score of 1.5 or more by comparison of a second disease group including a certain number of individuals having the same disease type as that of the first disease group or the first disease group with a third disease group including a certain number of individuals having a disease type different from that of the first disease group; forming clusters from pixels adjacent to one another among the extracted pixels; selecting a cluster having the largest size among the formed clusters as a second region cluster; forming a third region cluster from common pixels in the first region cluster and the second region cluster; and extracting the outline of the third region cluster.

11. The method according to claim 10, wherein the threshold is set by the following Formula (3) where S is the threshold, Anz2 is the average sum of z scores in the region of interest in the second image of normals, SDnz2 is the standard deviation of the sum of the z scores in the region of interest in the second image of the normals, and C is a constant between 1.5 and 1.6

[Formula (3)]

$$S = Anz2 + C \cdot SDnz2 \quad (3).$$

12. The method according to claim 10, wherein the threshold is set by the following Formula (4) where S is the threshold, Ant2 is the average sum of the t values in the region of interest in the second image of normals, SDnt2 is the standard deviation of the sum of the t values in the region of interest in the second image of the normals, and C is a constant between 1.5 and 1.6

[Formula (4)]

$$S = Ant2 + C \cdot SDnt2 \quad (4).$$

13. The method according to claim 10, wherein the disease type of the first and second disease groups is Dementia with Lewy body, the disease type of the third disease group is Alzheimer's disease, and the neurodegenerative disease is Dementia with Lewy body.

14. A non-transitory computer readable medium containing program instructions for detecting a neurological disease, wherein execution of the program instructions by one or more processors of a computer system causes the one or more processors to carry out the steps of:

a standardization step of creating a first image by applying anatomical standardization to a brain nuclear medical image;

a conversion step of creating a second image by converting the pixel value of each pixel of an image based on the first image into a z score or a t value;

an addition step of calculating the sum of the pixel values of individual pixels in a predetermined region of interest in the second image; and a determination step of obtaining the results of the determination of the neurodegenerative disease through an operation of comparison of the sum with a predetermined threshold, wherein the region of interest is preliminarily set as a region formed by extracting pixels having a z score of three or more obtained by comparison of a disease group having a certain number of individuals with a normal group having a certain number of individuals; forming clusters from pixels adjacent to one another among the extracted pixels; and selecting a cluster having the largest size among the formed clusters to extract the outline of the selected cluster.

15. The non-transitory computer readable medium of claim 14, wherein execution of the program instructions by one or more processors of a computer system causes the one or more processors to further carry out a normalization step of creating a normalized image by normalizing each pixel value of the first image, between the standardization step and the conversion step,
    enabling the conversion step to use the normalized image as the image based on the first image.

16. The non-transitory computer readable medium of claim 15, wherein execution of the program instructions by one or more processors of a computer system causes the one or more processors to further carry out the normalization step of creating the normalized image by calculating the average pixel value in a region corresponding to a primary sensorimotor area in the first image to normalize the pixel value of each pixel of the first image using the average.

17. A non-transitory computer readable medium containing program instructions for detecting a neurological disease, wherein execution of the program instructions by one or more processors of a computer system causes the one or more processors to carry out the steps of: a standardization step of creating a first image by applying anatomical standardization to a brain nuclear medical image;
    a conversion step of creating a second image by converting the pixel value of each pixel of an image based on the first image into a z score;
    an addition step of calculating the sum of the pixel values of individual pixels in a predetermined region of interest in the second image; and
    a determination step of obtaining the results of the determination of the neurodegenerative disease through an operation of comparison of the sum with a predetermined threshold, wherein the threshold is set by the following Formula (1) where S is the threshold, Anz is the average sum of the z scores in the region of interest in the second image of normals, SDnz is the standard deviation of the sum of the z scores in the region of interest in the second image of the normals, and C is a constant between 1.5 and 2.5
    [Formula (1)]

$$S = Anz + C \cdot SDnz \tag{1}$$

18. The non-transitory computer readable medium containing program instructions according to claim 17, wherein the constant C is in the range of 1.5 to 1.6.

19. A non-transitory computer readable medium containing program instructions for detecting a neurological disease, wherein execution of the program instructions by one or more processors of a computer system causes the one or more processors to carry out the steps of: a standardization step of creating a first image by applying anatomical standardization to a brain nuclear medical image;
    a conversion step of creating a second image by converting the pixel value of each pixel of an image based on the first image into a t value;
    an addition step of calculating the sum of the pixel values of individual pixels in a predetermined region of interest in the second image; and
    a determination step of obtaining the results of the determination of the neurodegenerative disease through an operation of comparison of the sum with a predetermined threshold, wherein the threshold is set by the following Formula (2) where S is the threshold, Ant is the average sum of t values in the region of interest in the second image of normals, SDnt is the standard deviation of the sum of the t values in the region of interest in the second image of the normals, and C is a constant between 1.5 and 2.0
    [Formula (2)]

$$S = Ant + C \cdot SDnt \tag{2}$$

20. The non-transitory computer readable medium containing program instructions according to claim 19, wherein the constant C is in the range of 1.5 to 1.6.

21. A non-transitory computer readable medium containing program instructions for detecting a neurological disease, wherein execution of the program instructions by one or more processors of a computer system causes the one or more processors to carry out the steps of: a standardization step of creating a first image by applying anatomical standardization to a brain nuclear medical image;
    a conversion step of creating a second image by converting the pixel value of each pixel of an image based on the first image into a z score or a t value;
    an addition step of calculating the sum of the pixel values of individual pixels in a predetermined region of interest in the second image; and
    a determination step of obtaining the results of the determination of the neurodegenerative disease through an operation of comparison of the sum with a predetermined threshold, wherein the region of interest is preliminarily set as a region formed by extracting a pixel having a Z score of 1.5 or more obtained by comparison of a first disease group including a certain number of individuals with a normal group including a certain number of individuals; forming clusters from pixels adjacent to one another among the extracted pixels; selecting a cluster having the largest size among the formed clusters as a first region cluster;
    extracting a pixel having a Z score of 1.5 or more by comparison of a second disease group including a certain number of individuals having the same disease type as that of the first disease group or the first disease group with a third disease group including a certain number of individuals having a disease type different from that of the first disease group; forming clusters from pixels adjacent to one another among the extracted pixels; selecting a cluster having the largest size among the formed clusters as a second region cluster; forming a third region cluster from common pixels in the first region cluster and the second region cluster; and extracting the outline of the third region cluster.

22. The non-transitory computer readable medium containing program instructions according to claim 21, wherein the threshold is set by the following Formula (3) where S is the threshold, Anz2 is the average sum of the z scores in the region of interest in the second image of normals, SDnz2 is the standard deviation of the sum of the z scores in the region of interest in the second image of the normals, and C is a constant between 1.5 and 1.6
    [Formula (3)]

$$S = Anz2 + C \cdot SDnz2 \tag{3}$$

23. The non-transitory computer readable medium containing program instructions according to claim 21, wherein the threshold is set by the following Formula (4) where S is the threshold, Ant2 is the average sum of the t values in the region of interest in the second image of normals, SDnt2 is the standard deviation of the sum of the t values in the region of interest in the second image of the normals, and C is a constant between 1.5 and 1.6
    [Formula (4)]

$$S = Ant2 + C \cdot SDnt2 \tag{4}$$

24. A neurodegenerative disease detector, comprising:
    standardization means of creating a first image by applying anatomical standardization to a brain nuclear medical image;

conversion means of creating a second image by converting the pixel value of each pixel of an image based on the first image into a z score or a t value;

addition means of calculating the sum of the pixel values of individual pixels in a predetermined region of interest in the second image; and determination means of obtaining the results of the determination of the neurodegenerative disease through an operation of comparison of the sum with a predetermined threshold, wherein the region of interest is preliminarily set as a region formed by extracting pixels having a z score of three or more obtained by comparison of a disease group having a certain number of individuals with a normal group having a certain number of individuals; forming clusters from pixels adjacent to one another among the extracted pixels; and selecting a cluster having the largest size among the formed clusters to extract the outline of the selected cluster.

25. The neurodegenerative disease detector of claim 24, further comprising normalization means of creating a normalized image by normalizing each pixel value of the first image, wherein the conversion means use the normalized image as the image based on the first image.

26. The detector according to claim 25, wherein the normalization means of creating a normalized image is performed by calculating the average pixel value in a region corresponding to a primary sensorimotor area in the first image to normalize the pixel value of each pixel of the first image using the average.

27. A neurodegenerative disease detector, comprising:
standardization means of creating a first image by applying anatomical standardization to a brain nuclear medical image;
conversion means of creating a second image by converting the pixel value of each pixel of an image based on the first image into a z score;
addition means of calculating the sum of the pixel values of individual pixels in a predetermined region of interest in the second image; and
determination means of obtaining the results of the determination of the neurodegenerative disease through an operation of comparison of the sum with a predetermined threshold wherein the threshold is set by the following Formula (1) where S is the threshold, Anz is the average sum of the z scores in the region of interest in the second image of normals, SDnz is the standard deviation of the sum of the z scores in the region of interest in the second image of the normals, and C is a constant between 1.5 and 2.5

[Formula (1)]

$$S = Anz + C \cdot SDnz \quad (1).$$

28. The detector according to claim 27, wherein the constant C is in the range of 1.5 to 1.6.

29. A neurodegenerative disease detector, comprising:
standardization means of creating a first image by applying anatomical standardization to a brain nuclear medical image;
conversion means of creating a second image by converting the pixel value of each pixel of an image based on the first image into a t value;
addition means of calculating the sum of the pixel values of individual pixels in a predetermined region of interest in the second image; and
determination means of obtaining the results of the determination of the neurodegenerative disease through an operation of comparison of the sum with a predetermined threshold, wherein the threshold is set by the following Formula (2) where S is the threshold, Ant is the average sum of t values in the region of interest in the second image of normals, SDnt is the standard deviation of the sum of the t values in the region of interest in the second image of the normals, and C is a constant between 1.5 and 2.0

[Formula (2)]

$$S = Ant + C \cdot SDnt \quad (2).$$

30. The detector according to claim 29, wherein the constant C is in the range of 1.5 to 1.6.

31. A neurodegenerative disease detector, comprising:
standardization means of creating a first image by applying anatomical standardization to a brain nuclear medical image;
conversion means of creating a second image by converting the pixel value of each pixel of an image based on the first image into a z score or a t value;
addition means of calculating the sum of the pixel values of individual pixels in a predetermined region of interest in the second image; and
determination means of obtaining the results of the determination of the neurodegenerative disease through an operation of comparison of the sum with a predetermined threshold, wherein the region of interest is preliminarily set as a region formed by extracting a pixel having a Z score of 1.5 or more obtained by comparison of a first disease group including a certain number of individuals with a normal group including a certain number of individuals; forming clusters from pixels adjacent to one another among the extracted pixels; selecting a cluster having the largest size among the formed clusters as a first region cluster;
extracting a pixel having a Z score of 1.5 or more by comparison of a second disease group including a certain number of individuals having the same disease type as that of the first disease group or the first disease group with a third disease group including a certain number of individuals having a disease type different from that of the first disease group; forming clusters from pixels adjacent to one another among the extracted pixels; selecting a cluster having the largest size among the formed clusters as a second region cluster; forming a third region cluster from common pixels in the first region cluster and the second region cluster; and extracting the outline of the third region cluster.

32. The detector according to claim 31, wherein the threshold is set by the following Formula (3) where S is the threshold, Anz2 is the average sum of the z scores in the region of interest in the second image of normals, SDnz2 is the standard deviation of the sum of the z scores in the region of interest in the second image of the normals, and C is a constant between 1.5 and 1.6

[Formula (3)]

$$S = Anz2 + C \cdot SDnz2 \quad (3).$$

33. The detector according to claim 31, wherein the threshold is set by the following Formula (4) where S is the threshold, Ant2 is the average sum of the t values in the region of interest in the second image of normals, SDnt2 is the standard deviation of the sum of the t values in the region of interest in the second image of the normals, and C is a constant between 1.5 and 1.6

[Formula (4)]

$$S = Ant2 + C \cdot SDnt2 \quad (4).$$

* * * * *